United States Patent
Pagani et al.

(10) Patent No.: US 6,342,632 B1
(45) Date of Patent: Jan. 29, 2002

(54) PROCESS AND PLANT FOR THE PRODUCTION OF UREA WITH HIGH CONVERSION YIELD AND LOW ENERGY CONSUMPTION

(75) Inventors: Giorgio Pagani, Lugano; Umberto Zardi, Breganzona, both of (CH)

(73) Assignee: Urea Casale, Lugano-Besso (CH)

( * ) Notice: Subject to any disclaimer, the term of this patent is extended or adjusted under 35 U.S.C. 154(b) by 214 days.

(21) Appl. No.: 08/860,960

(22) PCT Filed: Jan. 31, 1996

(86) PCT No.: PCT/IB96/00083

§ 371 Date: Jun. 24, 1997

§ 102(e) Date: Jun. 24, 1997

(87) PCT Pub. No.: WO96/23767

PCT Pub. Date: Aug. 8, 1996

(30) Foreign Application Priority Data

Feb. 1, 1995 (CH) ................................. 263/95

(51) Int. Cl.[7] ............................................. C07C 273/04
(52) U.S. Cl. ............................. 564/70; 564/67; 564/69; 564/71; 564/72
(58) Field of Search .............................. 564/67, 69, 70, 564/71, 72

(56) References Cited

U.S. PATENT DOCUMENTS

| 3,541,146 A | 11/1970 | Ledergerber et al. |
| 3,636,106 A | 1/1972 | Villiers-Fisher et al. |
| 4,354,040 A | 10/1982 | Inoue et al. ................... 564/67 |
| 4,504,679 A | 3/1985 | Inoue et al. ................... 564/67 |
| 5,763,660 A | 6/1998 | Rescalli |
| 5,886,222 A | 3/1999 | Rescalli |

FOREIGN PATENT DOCUMENTS

| EP | 0212744 | 8/1986 |
| GB | 1196657 | 7/1970 |
| GB | 1440624 | 6/1976 |
| WO | WO 99/29663 | 6/1999 |

OTHER PUBLICATIONS

Nitrogen, No. 157, Sep.–Oct. 1985, pp. 37–42.

Primary Examiner—Shailendra Kumar
(74) Attorney, Agent, or Firm—Sughrue Mion, PLLC (57) ABSTRACT

In a process for the production of urea, substantially pure ammonia and carbon dioxide are reacted in a reaction space (1) from which comes out a reaction mixture subjected to stripping (2) to obtain a partially purified mixture sent to a urea recovery section (3, 4, 7, 8). From the recovery section (3, 4, 7, 8) it is obtained a dilute carbamate solution, which is subjected to stripping (9) with recycling of vapors to the reaction space (1) after condensation (6). This process achieves high conversion yield with reduced energy consumption and low implementation costs.

40 Claims, 3 Drawing Sheets

PROCESS AND PLANT FOR THE PRODUCTION OF UREA WITH HIGH CONVERSION YIELD AND LOW ENERGY CONSUMPTION

This application is a 371 of PCT/IB95/00083, filed Jan. 13, 1996.

TECHNICAL FIELD

In its general aspect the present invention relates to a process for urea production.

The present invention relates specifically to a process for urea production of the type comprising the steps of:

- performing a reaction between ammonia and carbon dioxide in a reaction space to obtain a reaction mixture comprising urea, carbamate and free ammonia in aqueous solution;
- subjecting said mixture to a treatment of partial decomposition of the carbamate and partial separation of said free ammonia in aqueous solution to obtain a first flow comprising ammonia and carbon dioxide in vapor phase and a flow comprising urea and residual carbamate in aqueous solution;
- subjecting said first flow comprising ammonia and carbon dioxide in vapor phase to at least partial condensation to obtain a first portion of carbamate in aqueous solution;
- recycling said first portion of carbamate to said reaction space;
- feeding said flow comprising urea and residual carbamate in aqueous solution to a urea recovery section;
- separating in said recovery section said residual carbamate from the urea to obtain a second portion of carbamate in aqueous solution.

The present invention also relates to a plant for carrying out the above mentioned process and to a method for modernizing an existing urea plant to obtain a plant according to the present invention.

As known, in the field of urea production the need is ever more growing of plants having greater capacity and operating flexibility on the one hand, on the other hand, requiring ever smaller investment and operating costs, in particular in energy terms.

PRIOR ART

To this end, there have been proposed and implemented in the art a series of urea production processes essentially based on the performance of a conversion reaction in a reaction space fed with ammonia ($NH_3$) and carbon dioxide ($CO_2$) and to which are recycled the unreacted substances contained in the urea solution leaving the reaction space, in particular ammonia, carbon dioxide and carbamate in aqueous solution.

Figure 1:
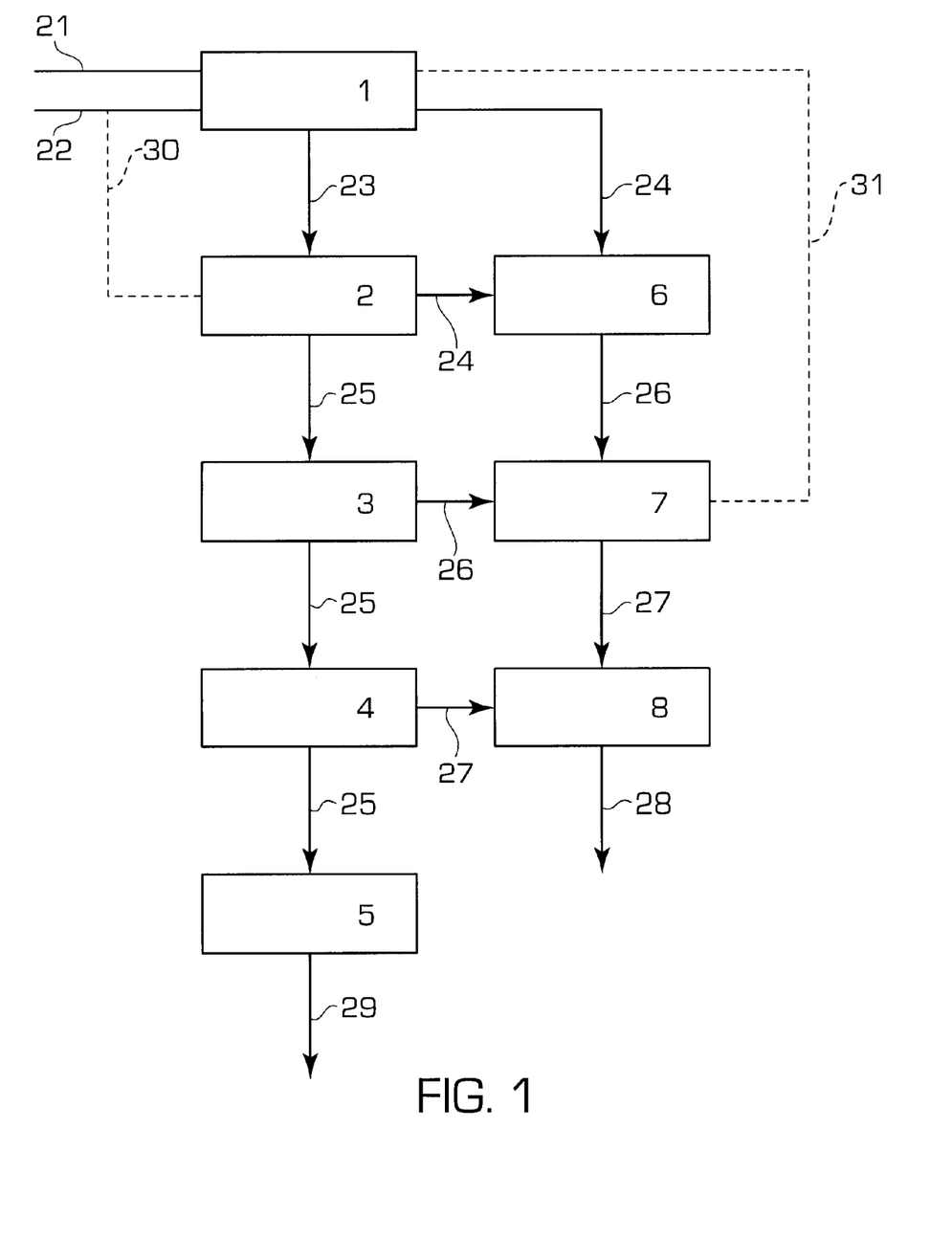
FIG. 1 shows a block diagram of a urea production process according the prior art.

A process of this type is shown in FIG. 1, and comprises downstream to a reaction space, a carbamate decomposition unit and a urea recovery section for separating from the urea solution the unreacted substances to be recycled.

If, on the one hand, this recycle allows almost complete recovery of valuable substances such as ammonia and carbon dioxide, on the other hand it also involves the sending to the reactor of large quantities of water ($H_2O$) which are detrimental to the overall yield of conversion of the carbon dioxide to urea, with the yield being generally between 59% and 63%.

SUMMARY OF THE INVENTION

The technical problem underlying the present invention is accordingly to conceive and make available a process for urea production achieving high conversion yield which would be technically simple to implement and would involve low investment and operating costs.

In accordance with the present invention, this problem is solved by a process of the above mentioned type which is characterized in that it comprises the additional steps of:

- subjecting at least part of said second portion of carbamate in aqueous solution obtained in said recovery section to a treatment of partial decomposition to obtain a second flow comprising ammonia and carbon dioxide in vapor phase and a flow comprising residual carbamate in aqueous solution;
- subjecting said second flow comprising ammonia and carbon dioxide in vapor phase to at least partial condensation to obtain a third portion of carbamate in aqueous solution;
- recycling said third portion of carbamate to said reaction space.

According to this invention, at least part of the carbamate in aqueous solution leaving the urea recovery section is advantageously subjected to a treatment of partial decomposition separating unreacted ammonia and carbon dioxide from a solution rich in water comprising residual carbamate.

So doing, the unreacted substances which are recycled to the reaction space have a very low water content, and thus it is possible to substantially limit the water fed to the reaction space, permitting a high conversion yield.

In order to obtain a high degree of decomposition of said at least part of the second portion of carbamate in aqueous solution, the same is preferably subjected to a decomposition treatment at a pressure substantially corresponding to the pressure in the reaction space.

To improve and assist the condensation and separation steps of the unreacted substances in the urea recovery section, the flow comprising residual carbamate in aqueous solution resulting from the treatment of partial decomposition of the second portion of carbamate is advantageously fed to said urea recovery section.

According to another embodiment of the present invention, the process comprises the steps of:

- feeding the reaction mixture comprising urea, carbamate and free ammonia in aqueous solution to a decomposition unit;
- feeding said at least part of the second portion of carbamate in aqueous solution to said decomposition unit, wherein the treatment of partial decomposition of the reaction mixture and of the second portion of carbamate is carried out advantageously in the same decomposition unit to obtain said first and second flow comprising ammonia and carbon dioxide in vapor phase and a flow comprising urea and residual carbamate in aqueous solution.

In accordance with this embodiment, the implementation of the urea production process is technically very simple, since no relevant additional equipment is required compared to the prior art processes, and it involves low investment costs.

Particularly satisfactory results have been obtained by subjecting at least 50% and preferably at least 65% of said second portion of carbamate in aqueous solution to the treatment of partial decomposition.

According to another aspect of the present invention, the technical problem set forth above is solved by a plant designed to implement the above mentioned urea production process comprising:

- a urea synthesis reactor;
- a first stripping unit for subjecting a reaction mixture leaving said reactor to a treatment of partial decomposition of the carbamate and partial separation of the free ammonia in aqueous solution present in said mixture;

means for condensing at least partially the vapors leaving said first stripping unit and of recycling a first portion of carbamate in aqueous solution to said reactor;

a recovery section of a flow comprising urea and residual carbamate in aqueous solution leaving said first stripping unit for separating the urea produced in the reactor from a second portion of carbamate in aqueous solution;

which plant is characterized in that it comprises:

a second stripping unit for subjecting at least part of said second portion of carbamate in aqueous solution to a treatment of partial decomposition;

means for condensing at least partially the vapors leaving said second stripping unit and of recycling a third portion of carbamate in aqueous solution to said reactor.

In accordance with a still further embodiment of the invention, the plant for urea production comprises:

a urea synthesis reactor;

a stripping unit for subjecting a reaction mixture leaving said first reactor to a treatment of partial decomposition of the carbamate and partial separation of the free ammonia in aqueous solution present in said mixture;

means for condensing at least partially the vapors leaving said stripping unit and of recycling a first portion of carbamate in aqueous solution to said first reactor;

a recovery section of a flow comprising urea and residual carbamate in aqueous solution leaving said stripping unit for separating the urea produced in the reactor from a second portion of carbamate in aqueous solution;

which plant is characterized in that it comprises:

means for feeding at least part of said second portion of carbamate in aqueous solution to the stripping unit.

In accordance with the present invention the plants delegated to carry out the urea production process may be provided either new or by modifying pre-existing plants so as to obtain a production capacity expansion and at the same time improved performance from the energy consumption viewpoint.

According to another aspect, the present invention accordingly makes available a method for modernizing a urea production plant of the type comprising:

a urea synthesis reactor;

a first stripping unit for subjecting a reaction mixture leaving said reactor to a treatment of partial decomposition of the carbamate and partial separation of the free ammonia in aqueous solution present in said mixture;

means for condensing at least partially the vapors leaving said first stripping unit and of recycling a first portion of carbamate in aqueous solution to said reactor;

a recovery section of a flow comprising urea and residual carbamate in aqueous solution leaving said first stripping unit for separating the urea produced in the reactor from a second portion of carbamate in aqueous solution;

which method is characterized in that it comprises the steps of:

providing a second stripping unit for subjecting at least part of said second portion of carbamate in aqueous solution to a treatment of partial decomposition;

providing means for condensing at least partially the vapors leaving said second stripping unit and of recycling a third portion of carbamate in aqueous solution to said reactor.

In an alternative embodiment, the modernization method of the present invention comprises the steps of:

providing a second stripping unit for subjecting at least part of said second portion of carbamate in aqueous solution to a treatment of partial decomposition;

providing means for feeding the vapors leaving said second stripping unit to said means for condensing the vapors leaving said first stripping unit.

According to a further embodiment, the modernization method of the present invention comprises the step of:

providing means for feeding at least part of said second portion of carbamate in aqueous solution to the stripping unit.

Further characteristics and advantages of the present invention are set forth in the detailed description of some preferred embodiments thereof given below by way of nonlimiting example with reference to the annexed drawings.

DETAILED DESCRIPTION OF THE PREFERRED EMBODIMENT

FIG. 1 shows a block diagram illustrating the steps of a urea production process according to the prior art.

Block 1 indicates a high pressure reaction space for the synthesis of urea which is fed by gas flows 21 and 22 comprising substantially pure ammonia and carbon dioxide respectively.

Typical operating conditions in the reaction space are:

molar ratio $NH_3/CO_2$ at input: 2.9 to 3.4;

molar ratio $H_2O/CO_2$ at input: 0.4 to 0.7;

conversion yield of the $CO_2$ into urea: 59% to 63%;

pressure: 150 bar a;

temperature: 185° C. to 190° C.

Blocks 2, 5 and 6 indicate respectively a high pressure decomposition unit, a urea granulation or prilling section and a high pressure condensation unit.

The decomposition and condensation units 2 and 6 generally operates at the same pressure conditions as the reaction space 1.

A urea recovery section is generally indicated by blocks 3, 4, 7 and 8. In particular, blocks 3 and 4 indicate a stripping or distillation unit and blocks 7 and 8 indicate a condensation unit.

Block 4 also indicates a urea finishing unit, wherein a solution with an urea content of up to 99.7% is obtained.

Block 8 also indicates a waste water treatment unit for purification of the water to be discharged from the urea production process.

Typically, blocks 3 and 7 operate at medium pressure (about 18 bar), while blocks 4 and 8 operate at low pressure (about 4 bar).

Flow line 23 represents a liquid flow of a reaction mixture coming from block 1 and comprising urea and unreacted substances, notably carbamate and free ammonia in aqueous solution.

The liquid flow 23 is fed to block 2, where it is subjected to a treatment of partial decomposition of the carbamate and partial separation of the free ammonia.

The decomposition unit indicated by block 2 generally comprises a stripper apparatus which operates with a flow 30 of carbon dioxide as stripping agent coming from the flow line 22.

At the outlet of block 2, flow lines 24 and 25 are shown which represent respectively a gas flow comprising ammonia and carbon dioxide in vapor phase and a liquid flow comprising urea and residual carbamate in aqueous solution.

Flow line 24 traverses the condensation unit represented by block 6, where the ammonia and carbon dioxide in vapor phase are condensed obtaining a flow of carbamate in aqueous solution which is recycled to the reaction space 1.

The flow comprising urea and residual carbamate in aqueous solution indicated by flow line 25 traverses the distillation units of the urea recovery section indicated by blocks 3 and 4, where the residual carbamate is decomposed and separated from the urea solution.

Generally, the urea content in the liquid flow 25 is between 70%–72% after block 3 and about 99% after block 4.

Flow lines 26 and 27 represent a gas flow comprising ammonia and carbon dioxide in gaseous phase obtained in blocks 3 and 4 respectively.

The flow 27 traverses the condensation unit represented by block 8, where the ammonia and carbon dioxide in vapor phase are condensed obtaining a flow of carbamate in aqueous solution, and is fed to the condensation unit 7, where it promotes condensation of the gas flow 26.

Analogously, the flow 26 traverses the condensation unit represented by block 7, where the ammonia and carbon dioxide in vapor phase are condensed obtaining a flow of carbamate in aqueous solution, and is fed to the condensation unit 6, where it promotes condensation of the gas flow 24.

Part of the water contained in the aqueous solution obtained in the condensation unit of block 8 is further treated and purified of almost all traces of ammonia and urea in the treatment unit also indicated by block 8. From block 8 departs a flow line 28 of a waste water flow to be discharged from the urea production process.

Finally, the urea solution flow 25 coming from block 4 traverses the granulation or prilling section indicated by block 5, where it is transformed to a final product leaving the urea production process by flow line 29.

In accordance with an alternative embodiment of the prior art process, block 7 also indicates an ammonia separation column to obtain a substantially pure liquid ammonia which is sent to the reaction space 1 in addition to the flow 21, as indicated by flow line 31 in FIG. 1.

As shown in FIG. 1, in the urea production process according to the prior art, all the carbamate containing aqueous solution separated from the urea is recycled to the reaction space 1, with the large amount of water therein contained being used for condensation and conveyance of the unreacted substances.

Figure 2:
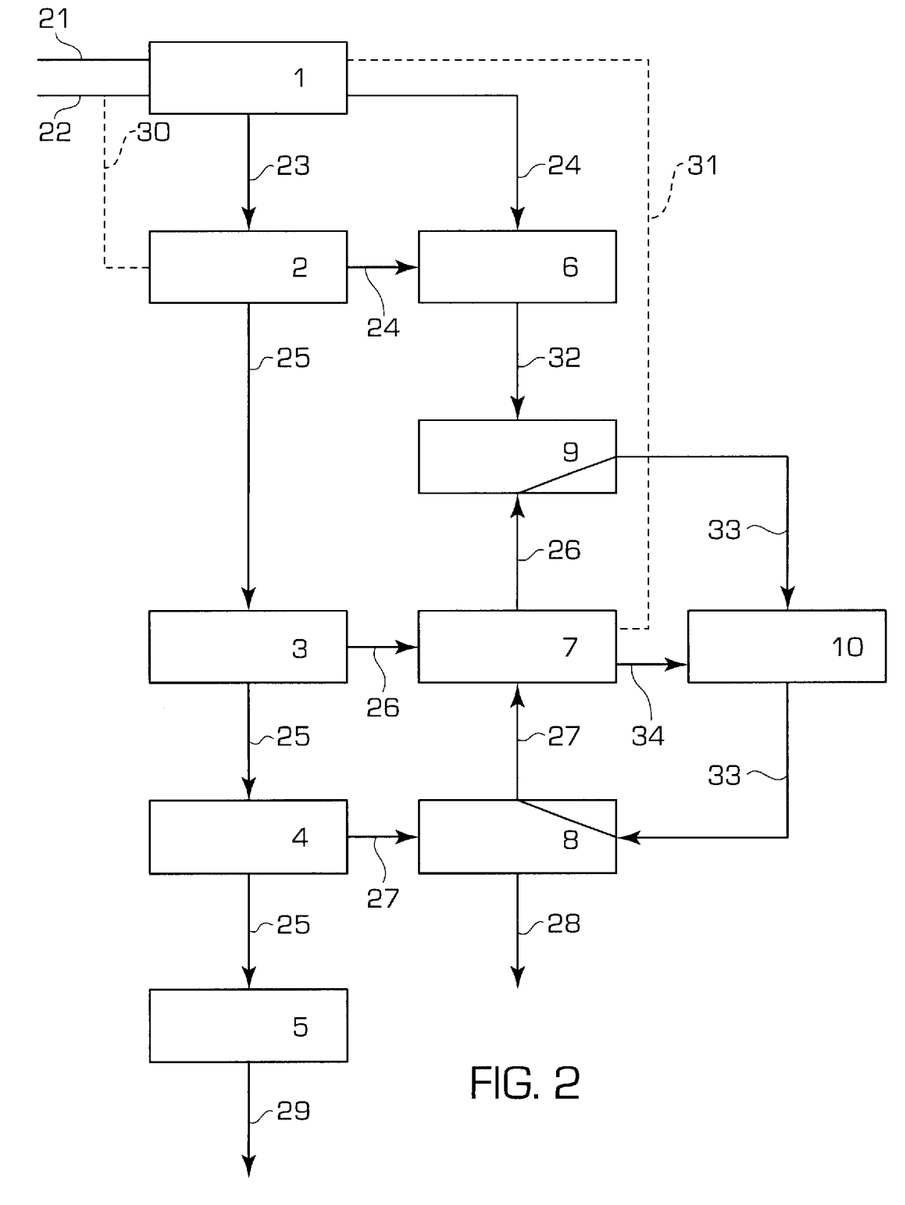
FIG. 2 shows a block diagram of a first embodiment of the urea production process according to present invention.
Figure 3:
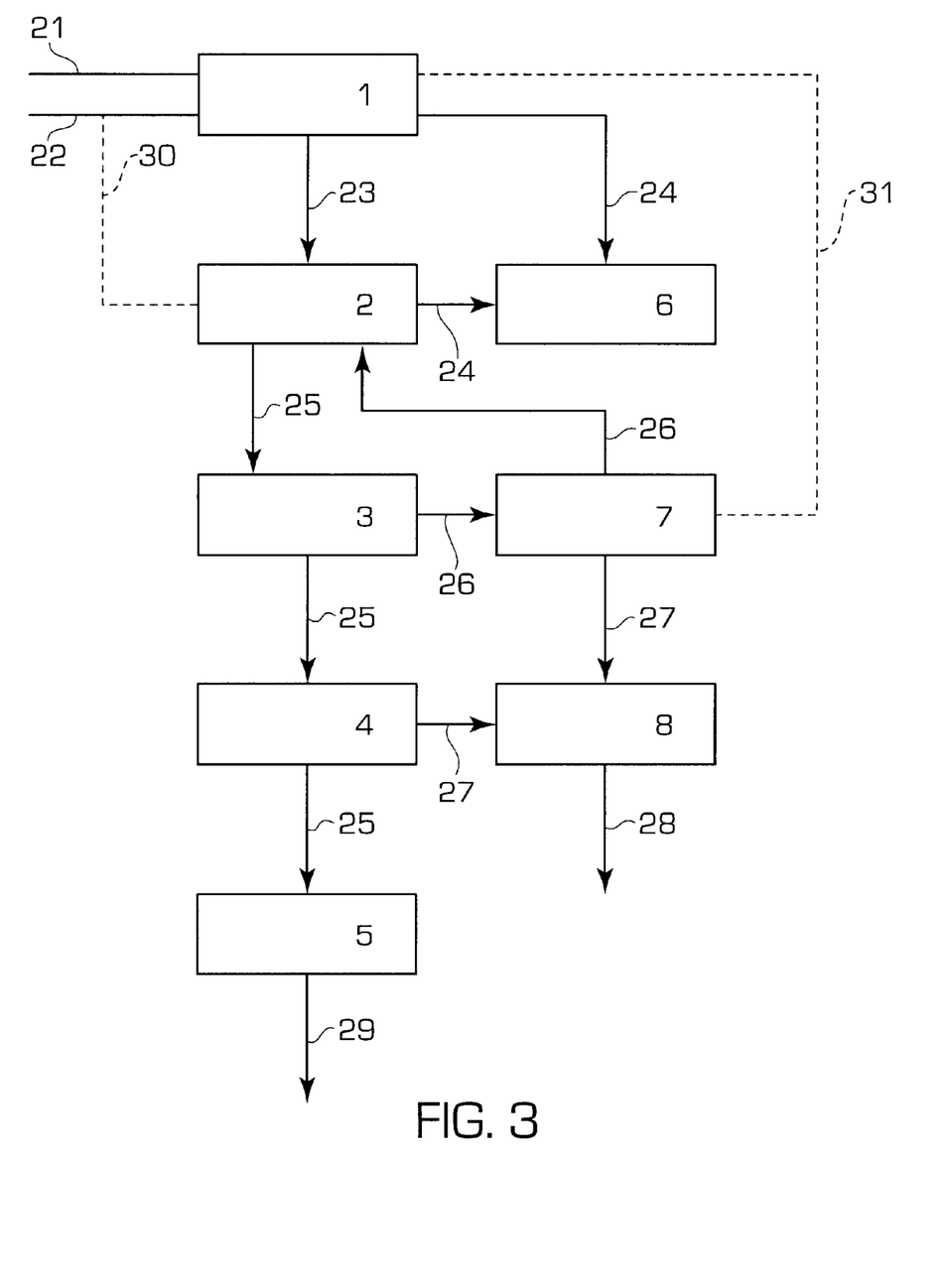
FIG. 3 shows a block diagram of a second embodiment of the urea production process according to the present invention.

In FIGS. 2 and 3, it is indicated a block diagram of a first respectively second embodiment of the urea production process according to the present invention.

In said figures the details of the block diagram structurally and functionally equivalent to those shown in FIG. 1 are indicated by the same reference numbers and not further described.

In FIG. 2, block 9 indicates a high pressure decomposition unit operating at the same pressure conditions as the reaction space 1.

The liquid flow 26 containing carbamate in aqueous solution and having a high water content is fed to block 9, where it is advantageously subjected to a treatment of partial decomposition of the carbamate.

At the outlet of block 9, flow lines 32 and 33 are shown which represent respectively a gas flow comprising ammonia and carbon dioxide in vapor phase and a liquid flow comprising urea and residual carbamate in aqueous solution.

The gas flow 32, which is very rich in ammonia and carbon dioxide and poor in water (only a few percentages points), traverses the condensation unit represented by block 6, where ammonia and carbon dioxide are condensed obtaining a flow of carbamate in aqueous solution, and is recycled to the reaction space 1 through flow line 24.

In the example of FIG. 2, all the carbamate in aqueous solution separated from the urea in the recovery section is subjected to the decomposition treatment in block 9. However, satisfactory results have been obtained also by feeding to block 9 only a part of carbamate leaving the urea recovery section. Preferably, at least 50% of this carbamate may be sent to block 9.

According to the process of the present invention, a reaction between ammonia and carbon dioxide is performed in reaction space 1 obtaining a reaction mixture comprising urea, carbamate and free ammonia in aqueous solution, which is subjected in decomposition unit 2 to a treatment of partial decomposition of the carbamate and partial separation of said free ammonia in aqueous solution. From the decomposition unit 2 departs a first flow 24 comprising ammonia and carbon dioxide in vapor phase and a flow 25 comprising urea and residual carbamate in aqueous solution. The flow 24 is then subjected to at least partial condensation in block 6 to obtain a first portion of carbamate in aqueous solution which is recycled to the reaction space 1. The flow 25 is on the contrary fed to a urea recovery section (blocks 3, 4, 7 and 8) where the urea is separated from a second portion of carbamate in aqueous solution indicated by flow line 26.

Advantageously, in accordance with other process steps of the present invention, at least part of the flow 26 is further subjected to a treatment of partial decomposition in block 9 to obtain a second flow 32 comprising ammonia and carbon dioxide in vapor phase and a flow 33 comprising residual carbamate in aqueous solution. The flow 32 is then at least partially condensed in block 6 to obtain a third portion of carbamate in aqueous solution recycled to the reaction space via flow line 24.

By operating in this manner it is possible to obtain a high conversion yield in the reaction space since a highly concentrated solution of carbamate which is very poor in water is recycled to the same.

According to the present urea production process, it is possible to achieve a conversion yield of carbon dioxide to urea of about 70% to 75%, which is notably greater than that obtainable with the prior art processes.

Moreover, this high conversion yield and the substantially absence of water to be recycled to the reaction space 1 also result in a smaller flow of substances to be separated from the urea solution, and thus it result in an increase in the performance of the decomposition unit 2 and of the distillation units 3 and 4 of the recovery section.

In the example of FIG. 2, the liquid flow 33, which is very rich in water, is advantageously recycled to the urea recovery section in order to promote condensation and recover of the unreacted substances which are freed in the distillation units 3 and 4.

Preferably, flow line 33 traverses a distillation unit indicated by block 10, where the residual carbamate is further subjected to decomposition in order to obtain a solution very rich in water which is fed to block 8.

From block 10 also departs a flow line 34 of a water poor vapor flow comprising residual ammonia and carbon dioxide which is fed to the condensation unit indicated by block 7 of the recovery section.

There is thus obtained a separate circulation loop of process water which advantageously promotes condensation of ammonia and carbon dioxide vapors in units 7 and 8 without being recycled to the reaction space 1 and thus without negatively affecting the reaction between ammonia and carbon dioxide.

In the alternative embodiment of the process according to the present invention disclosed in FIG. 3, the flow line 26 coming from the urea recovery section, namely the condensation unit 7, instead of being recycled directly to the reaction space 1 through block 6 as in the prior art process, it is advantageously fed to the decomposition unit indicated by block 2, where a flow of ammonia and carbon dioxide in vapor phase is obtained which is recycled via flow line 24 to the reaction space 1 after condensation in the block 6.

So doing, the treatment of partial decomposition of the second portion of carbamate in aqueous solution (flow 26) is carried out in the same decomposition unit of the reaction mixture (flow 23), thereby permitting an implementation of the process according to the present invention which does not require the use of relevant additional equipment if compared to the prior art.

As stripping agents for the decomposition unit 2 it can also be used a part of the ammonia flow fed to the reaction space. Alternatively, the block 2 can be operated in a self-stripping mode, wherein the evaporated ammonia promotes the decomposition of the carbamate.

Moreover, the urea recovery section may only comprises the low pressure units 4 and 8. In this case, the flow comprising urea and residual carbamate in aqueous solution coming from the decomposition unit 2 is fed directly to block 4 for final separation of the urea solution from the unreacted substances.

Reference is now made to a plant for urea production specifically designed to carry out the process according to the present invention.

The urea production plant advantageously comprises a urea synthesis reactor indicated by block 1, a first and a second stripping unit indicated by blocks 2 and 9 respectively, a urea recovery section indicated by blocks 3, 4, 7 and 8, and respective means for condensing and recycling to the reactor the vapors leaving the first and the second stripping unit.

With reference to the embodiment of FIG. 2, the means for condensing the vapors leaving the second stripping unit 9 preferably comprises the means for condensing the vapors leaving the first stripping unit 2 and is indicated by block 6.

A distiller unit indicated by block 10 is also disposed between the second stripping unit and the recovery section.

With reference to the embodiment of FIG. 3, the urea production plant comprises feeding means indicated by flow line 26 between the recovery section and the stripping unit 2. In this case the stripping unit 9 and the distiller unit 10 are not needed.

The plant designed to implement the process for urea production in accordance with the present invention may be a brand new plant or a plant obtained by modernizing a pre-existing plant such as the plant resulting from the implementation of the process illustrated in the block diagram of FIG. 1.

According to a first embodiment, this modernization takes place by means for the steps of:

providing a second stripping unit (block 9) for subjecting at least part of the carbamate in aqueous solution leaving the recovery section (flow line 26) to a treatment of partial decomposition;

providing means for condensing at least partially the vapors leaving said second stripping unit and of recycling the so obtained high concentrated carbamate solution to the reactor (block 1).

In accordance with another embodiment of the invention, the modernizing method preferably comprises the step of:

providing means for feeding the vapors leaving the second stripping unit (block 9) directly to the means for condensing the vapors leaving the first stripping unit 2, represented by block 6.

Advantageously, the method for modernizing a pre-existing plant additionally comprise the step of:

providing means for feeding (flow line 33) a flow comprising residual carbamate in aqueous solution from the second stripping unit (block 9) to the urea recovery section.

In a particular and advantageous embodiment of the present invention, the modernizing method comprises the step of:

providing means for feeding (flow line 26) at least part of the carbamate solution coming from the urea recovery section to the stripping unit indicated by block 2.

Thanks to the modernizing method of the present invention, not only the conversion yield of the pre-existing urea synthesis reactor can be drastically increased but also its capacity.

In fact, since only a very small amount of water is recycled to the reactor 1, a bigger flow of ammonia and carbon dioxide may be fed to the same without causing a capacity overcharge in the reactor itself as well as in the decomposition unit 2 and in the distillation units 3 and 4 of the recovery section.

In the next examples there are compared by way of merely indicative and non limiting example the conversion yields obtainable by a plant implementing the process according to the present invention or modernized by the method of the present invention and by a plant implementing the process according to the prior art.

EXAMPLE 1

A pre-existing plant operating according to the prior art process described with reference to FIG. 1 is modernized in order to operate according to the process described with reference to FIG. 2.

The pre-existing plant is based on the so-called ammonia self-stripping process, wherein no ammonia or carbon dioxide stripping agent is fed to the decompostion unit indicated by block 2. Therefore, in this case flow line 30 is missing.

The operation conditions of the urea synthesis reactor before the plant modernization are the followings:

molar ratio $NH_3/CO_2$ at input: 3.2;

molar ratio $H_2O/CO_2$ at input: 0.6;

conversion yield of the $CO_2$ into urea: 61%;

pressure: about 150 bar a;

temperature: 190° C.;

capacity: 1800 MTD urea

After modernizing the pre-existing plant by providing a second stripping unit 9 fed with 77% of the carbamate solution coming from the urea recovery section, and by feeding the vapors leaving said second stripping unit to the reactor space 1 via the condenser unit 6, as described with reference to FIG. 2, the new operating conditions of the reactor are the followings:

molar ratio $NH_3/CO_2$ at input: 3.2;
molar ratio $H_2O/CO_2$ at input: 0.19;
conversion yield of the $CO_2$ into urea: 70%;
pressure: about 150 bar a;
temperature: 190° C.;
capacity: 2500 MTD urea Thanks to the present invention, it is possible to increase the conversion yield of 9 points percentage and to increase the capacity of 700 MTD urea, i.e. 39% more than the original capacity.

Such a relevant increase in the conversion yield and the much lower amount of water recycled to the reactor allow to obtain the new increased capacity with only minor modifications to the pre-existing plant and with low investment costs. Moreover, this high conversion yield also results in a reduction in energy consumption of the modernized plant.

EXAMPLE 2

A pre-existing plant operating according to the prior art process described with reference to FIG. 1 is modernized in order to operate according to the process described with reference to FIG. 2.

The pre-existing plant is based on the carbon dioxide stripping process, wherein a flow of carbon dioxide as stripping agent is fed to the decompostion unit indicated by block 2 (flow line 30). In this case, the ammonia separation unit comprised in block 7 and flow line 31 are missing. Also units 3 and 7 are missing, and the urea recovery section only comprises the low pressure units 4 and 8.

The operation conditions of the urea synthesis reactor before the plant modernization are the followings:

molar ratio $NH_3/CO_2$ at input: 3.0;
molar ratio $H_2O/CO_2$ at input: 0.5;
conversion yield of the $CO_2$ into urea: about 60%;
pressure: about 145 bar a;
temperature: 185° C.;
capacity: 1900 MTD urea After modernizing the pre-existing plant by providing a second stripping unit 9 fed with 70% of the carbamate solution coming from the urea recovery section, and by feeding the vapors leaving said second stripping unit to the reactor space 1 via the condenser unit 6, as described with reference to FIG. 2, the new operating conditions of the reactor are the followings:

molar ratio $NH_3/CO_2$ at input: 3.0;
molar ratio $H_2O/CO_2$ at input: 0.25;
conversion yield of the $CO_2$ into urea: 66%;
pressure: about 150 bar a;
temperature: 190° C.;
capacity: 2500 MTD urea Thanks to the present invention, it is possible to increase the conversion yield of 6 points percentage and to increase the capacity of 600 MTD urea, i.e. 32% more than the original capacity.

Also in this case, only minor modifications to the pre-existing plant and low investment costs are required to obtain a relevant increase in the capacity and the conversion yield.

EXAMPLE 3

In this example, the conversion yield of a reactor operating in a brand new plant implementing the process according to the present invention as described in FIG. 2 has been simulated.

As for the above example 2, the plant is based on the carbon dioxide stripping process, wherein all the carbon dioxide to be fed to the reactor 1 is first fed as stripping agent in the decompostion unit indicated by block 2 through flow line 30. In this case, flow line 22 is missing as well as the ammonia separation unit comprised in block 7 and flow line 31. The urea recovery section comprises the medium and low pressure units 3, 4, 7 and 8.

The operation conditions of the reactor in the urea production plant according to the present invention are the followings:

molar ratio $NH_3/CO_2$ at input: 3.2;
molar ratio $H_2O/CO_2$ at input: 0.1;
pressure: about 150 bar a;
temperature: 190° C.;
capacity: 400 MTD urea The conversion yield of the $CO_2$ into urea obtained by the present reactor is very high: 72%. Moreover, the content of water in the carbamate solution recycled to the reactor is particularly low.

Since low amounts of water and unreacted substances are contained in the reaction mixture sent to the decomposition unit and further to the recovery section, it results that the duties of the process equipment are lower if compared to the conventional plants and consequently also the energy consumption and the investment costs.

The results given in the above examples have been obtained by means for well known calculation algorithms.

What is claimed is:

1. A process for urea production, comprising the steps of:

reacting ammonia and carbon dioxide in a reaction space to obtain a reaction mixture comprising urea, carbamate and free ammonia in aqueous solution;

subjecting said mixture to a treatment of partial decomposition of the carbamate and partial separation of said free ammonia in aqueous solution to obtain a first flow comprising ammonia and carbon dioxide in vapor phase and a flow comprising urea and residual carbamate in aqueous solution;

subjecting said first flow comprising ammonia and carbon dioxide in vapor phase to at least partial condensation to obtain a first portion of carbamate in aqueous solution;

recycling said first portion of carbamate to said reaction space;

feeding said flow comprising urea and residual carbamate in aqueous solution to a urea recovery section;

separating in said recovery section said residual carbamate from the urea to obtain a second portion of carbamate in aqueous solution;

subjecting at least part of said second portion of carbamate in aqueous solution obtained in said recovery section to a treatment of partial decomposition to obtain a second flow comprising ammonia and carbon dioxide in vapor phase and a flow comprising residual carbamate in aqueous solution;

subjecting said second flow comprising ammonia and carbon dioxide in vapor phase to at least partial condensation to obtain a third portion of carbamate in aqueous solution; and recycling said third portion of carbamate to said reaction space.

2. Process according to claim 1, characterized in that the treatment of partial decomposition of the said at least part of the second portion of carbamate in aqueous solution is carried out at a pressure substantially corresponding to the pressure in the reaction space.

3. Process according to claim 1, characterized in that it further comprises the step of:

feeding the flow comprising residual carbamate in aqueous solution resulting from the treatment of partial decomposition of the second portion of carbamate to said urea recovery section.

4. A process according to claim 1, further comprising the steps of:

feeding said reaction mixture comprising urea, carbamate and free ammonia in aqueous solution to a decomposition unit;

feeding said at least part of said second portion of carbamate in aqueous solution to said decomposition unit, wherein said partial decomposition treatment of said reaction mixture and of said second portion of carbamate is carried out in said decomposition unit to obtain said first and second flow comprising ammonia and carbon dioxide in vapor phase and a flow comprising urea and residual carbamate in aqueous solution.

5. Process according to claim 1, characterized in that at least 50% of said second portion of carbamate in aqueous solution is subjected to the treatment of partial decomposition.

6. Process according to claim 5, characterized in that at least 65% of said second portion of carbamate in aqueous solution is subjected to the treatment of partial decomposition.

7. A process for urea synthesis from ammonia and carbon dioxide, with ammonium carbamate being formed as an intermediate species, which comprises the following steps:

(a) feeding a stream comprising ammonia and carbon dioxide to a reaction space and causing them to react with each other, with a molar ratio of $NH_3:CO_2$ within the range of from 2.9 to 3.4, to form a first liquid mixture containing urea, carbamate, water and ammonia, wherein the average molar ratio of $H_2O:CO_2$ in the feed stream to said reaction space is from 0.1 to 0.25;

(b) transferring said first liquid mixture to a first decomposition-stripping step;

(c) heating said first liquid mixture in said first decomposition-stripping step, said first decomposition-stripping step operating under substantially the same pressure as existing in said reaction space, to cause a portion of carbamate contained in said first liquid mixture to decompose into ammonia and carbon dioxide, and simultaneously stripping said first liquid mixture to form a first gas mixture containing ammonia and carbon dioxide, and a second liquid mixture containing urea, water, ammonia, and an undecomposed portion of carbamate;

(d) transferring said first gas mixture to a condensation step operating under substantially the same pressure as in said reaction space and condensing said mixture, to form a third liquid mixture which contains carbamate and ammonia, which third liquid mixture is recycled to said reaction space of step (a);

(e) recovering urea contained in said second liquid mixture in one or more subsequent decomposition/separation step(s) to provide urea and a fourth liquid mixture containing water, ammonia and carbamate, wherein at least 50% of said fourth liquid mixture formed in step (e) is sent to said first decomposition-stripping step.

8. A process according to claim 7, in which said first decomposition-stripping step operates under self-stripping conditions.

9. A process according to claim 7, in which fresh carbon dioxide is at least partially directly fed to said first decomposition-stripping step.

10. A process according to claim 7, in which said reaction space operates at a temperature within the range of from 185° C. to 190° C.

11. A process according to claim 10, in which said reaction space operates at a temperature of 190° C.

12. A process according to claim 11, in which said reaction space operates at a pressure of 150 bar a.

13. A process according to claim 11, in which said reaction space operates at a pressure of 150 bar a.

14. A process according claim 7, in which carbon dioxide conversion is within the range of from 66 to 75% per cycle.

15. A process according to claim 14, in which said carbon dioxide conversion is within the range of from 70 to 75% per cycle.

16. A process according to claim 15, in which said carbon dioxide conversion is within the range of 72 to 75% per cycle.

17. A process according to claim 7, in which at least 65% of said fourth liquid formed in step (e) is sent to said first decomposition-stripping step.

18. A process according to claim 17, in which at least 70% of said fourth liquid formed in step (e) is sent to said first decomposition-stripping step.

19. A process according to claim 17, in which at least 77% of said fourth liquid formed in step (e) is sent to said first decomposition-stripping step.

20. A process according to claim 7, wherein said reaction space is a reactor.

21. A process according to claim 7, wherein said molar ratio of $NH_3:CO_2$ is within the range of 3.0 to 3.2.

22. A process according to claim 7, wherein said carbamate is ammonium carbamate.

23. A process according to claim 7, wherein said average molar ratio of $H_2O:CO_2$ in the feed stream to said reaction space is from 0.1 to 0.19.

24. A process for urea synthesis from ammonia and carbon dioxide, with ammonium carbamate being formed as an intermediate species, which comprises the following steps:

(a) feeding ammonia and carbon dioxide to a reaction space and causing them to react with each other, with a molar ratio of $NH_3:CO_2$ within the range of 2.9 to 3.4, with a first liquid mixture containing urea, carbamate, water and ammonia being formed;

(b) transferring said first liquid to a first decomposition-stripping step;

(c) heating said first liquid mixture in said first decomposition-stripping step, said first decomposition-stripping step operating under substantially the same pressure as existing in said reaction space, to cause a portion of carbamate contained in said first liquid mixture to decompose into ammonia and carbon dioxide, and simultaneously stripping said first liquid mixture to form a first gas mixture containing ammonia and carbon dioxide, and a second liquid mixture containing urea, water, ammonia, and an undecomposed portion of carbamate;

(d) transferring said first gas mixture to a condensation step operating under substantially the same pressure as in said reaction space and condensing said mixture, to form a third liquid mixture which contains carbamate and ammonia, which third liquid mixture is recycled to said reaction space of step (a);

(e) recovering urea contained in said second liquid mixture in one or more subsequent decomposition/separation step(s) to provide urea, a fourth liquid mixture containing water, ammonia and carbamate, and a fifth stream containing ammonia, wherein at least 50% of said fourth liquid mixture formed in step (e) is sent to said first decomposition-stripping step.

25. A process according to claim 24, in which said first decomposition-stripping step operates under self-stripping conditions.

26. A process according to claim 24, in which fresh carbon dioxide is at least partially directly fed to said first decomposition-stripping step.

27. A process according to claim 24, in which said reaction space operates at a temperature within the range of from 185° C. to 190° C.

28. A process according to claim 27, in which said reaction space operates at a temperature of 190° C.

29. A process according to claim 27, in which said reaction space operates at a pressure of 150 bar a.

30. A process according to claim 28, in which said reaction space operates at a pressure of 150 bar a.

31. A process according claim 24, in which carbon dioxide conversion is within the range of from 66 to 75% per cycle.

32. A process according to claim 31, in which said carbon dioxide conversion is within the range of from 70 to 75% per cycle.

33. A process according to claim 32, in which said carbon dioxide conversion is within the range of 72 to 75% per cycle.

34. A process according to claim 24, in which at least 65% of said fourth liquid formed in step (e) is sent to said first decomposition-stripping step.

35. A process according to claim 34, in which at least 70% of said fourth liquid formed in step (e) is sent to said first decomposition-stripping step.

36. A process according to claim 35, in which at least 77% of said fourth liquid formed in step (e) is sent to said first decomposition-stripping step.

37. A process according to claim 24, wherein said reaction space is a reactor.

38. A process according to claim 24, wherein said molar ratio of $NH_3:CO_2$ is within the range of 3.0 to 3.2.

39. A process according to claim 24, wherein said carbamate is ammonium carbamate.

40. A process according to claim 24, wherein said fifth stream containing urea is recycled to said reaction space.

* * * * *

UNITED STATES PATENT AND TRADEMARK OFFICE
CERTIFICATE OF CORRECTION

PATENT NO. : 6,342,632 B1
DATED : January 29, 2002
INVENTOR(S) : Pagani et al.

It is certified that error appears in the above-identified patent and that said Letters Patent is hereby corrected as shown below:

<u>Title page,</u>
Item [*] Notice, "214" and insert -- 139 --.

Signed and Sealed this

Nineteenth Day of August, 2003

JAMES E. ROGAN
*Director of the United States Patent and Trademark Office*